US012702413B2

(12) United States Patent
Nicholas et al.

(10) Patent No.: US 12,702,413 B2
(45) Date of Patent: Aug. 11, 2026

(54) POWERED SURGICAL DEVICE WITH LINEAR POSITION SENSOR

(71) Applicant: Covidien LP, Mansfield, MA (US)

(72) Inventors: David A. Nicholas, Trumbull, CT (US); Anthony D. Calderoni, Bristol, CT (US); John M. Pantazis, Stratford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/123,469

(22) PCT Filed: Oct. 19, 2023

(86) PCT No.: PCT/IB2023/060565
§ 371 (c)(1),
(2) Date: Apr. 23, 2025

(87) PCT Pub. No.: WO2024/089546
PCT Pub. Date: May 2, 2024

(65) Prior Publication Data

US 2026/0144545 A1 May 28, 2026

Related U.S. Application Data

(60) Provisional application No. 63/420,304, filed on Oct. 28, 2022.

(51) Int. Cl.
*A61B 17/072* (2006.01)
*A61B 90/00* (2016.01)
*A61B 17/00* (2006.01)

(52) U.S. Cl.
CPC ........ *A61B 17/07207* (2013.01); *A61B 90/03* (2016.02); *A61B 2017/00398* (2013.01); *A61B 2090/034* (2016.02)

(58) Field of Classification Search
CPC .............. A61B 17/07207; A61B 90/03; A61B 2090/034; A61B 2017/00398
See application file for complete search history.

(56) References Cited

U.S. PATENT DOCUMENTS 6,684,470 B1 * 2/2004 Joux ...................... B21J 15/105
29/243.526
8,523,043 B2 * 9/2013 Ullrich ................. A61B 17/072
227/19

(Continued)

FOREIGN PATENT DOCUMENTS

EP 2792308 A2 10/2014

OTHER PUBLICATIONS

PCT/IB2023/060565, The International Search Report and Written Opinion, mailed Jan. 25, 2024, 12pages.

*Primary Examiner* — Himchan Song

(57) ABSTRACT

A powered surgical device includes a handle assembly that includes a linear position sensor in the form of a linear potentiometer for identifying a position of a rack within the handle assembly. The linear potentiometer provides a signal indicative of the position of the rack to a controller to control operation of a motor or motors positioned within the handle assembly to control various functions of the surgical device. The linear potentiometer supports a lever assembly that is coupled to a slide of the linear potentiometer to selectively couple and decouple the slide from the rack. The lever assembly facilitates the use of a linear potentiometer having a shorter length.

20 Claims, 10 Drawing Sheets

(56) References Cited

U.S. PATENT DOCUMENTS 8,733,614 B2 * 5/2014 Ross .................... A61B 17/068
227/179.1
8,960,520 B2 * 2/2015 McCuen .............. A61B 17/068
227/175.1
8,967,443 B2 * 3/2015 McCuen ................ A61B 34/76
227/175.1
9,113,880 B2 * 8/2015 Zemlok ............ A61B 17/07207
10,111,657 B2 10/2018 McCuen
10,498,269 B2 12/2019 Zemlok et al.
10,779,820 B2 * 9/2020 Harris .................. A61B 17/068
2014/0305987 A1 * 10/2014 Parihar .............. A61B 17/0686
227/175.2
2016/0184040 A1 * 6/2016 Sholev ............. A61B 17/00234
606/130
2017/0245854 A1 * 8/2017 Zemlok ............ A61B 17/07207
2017/0290583 A1 * 10/2017 Reed ................ A61B 17/07207
2019/0125389 A1 * 5/2019 Shelton, IV ....... A61B 17/1285
2021/0045764 A1 * 2/2021 Sholev ................... A61B 34/71

* cited by examiner 60
102
62
104
110
110

84a
92
90
84b
82
86
94
88
98
96
56
80
58

32
84a
12
100
F
18
102
104
62
B
56
22
94
96
84b
A
112
80

32
12
62
102
84a
104
100
62
30
94
96
92
90
84b 14
16
50
48
52
54
D

84a
H
96
94
18
12
90
92
K
104
62
J
84b
100
H
G
22
I

POWERED SURGICAL DEVICE WITH LINEAR POSITION SENSOR

CROSS-REFERENCE TO RELATED APPLICATIONS

This application is a National Stage Application of PCT/IB2023/060565 filed 19 Oct. 2023, which claims benefit of and priority to U.S. Provisional Application No. 63/420,304 filed 28 Oct. 2022, and the disclosures of each of the above-identified applications are hereby incorporated by reference in their entirety.

FIELD

This disclosure is directed to powered surgical devices and, more particularly, to powered surgical stapling devices with a linear position sensor.

BACKGROUND

Various types of surgical devices used to endoscopically treat tissue are known in the art, and are commonly used, for example, for closure of tissue or organs in transection, resection, and anastomoses procedures, for occlusion of organs in thoracic and abdominal procedures, and for electrosurgically fusing or sealing tissue.

One example of such a surgical device is a surgical stapling device. Typically, surgical stapling devices include a tool assembly having an anvil assembly and a cartridge assembly, and a firing actuator. The cartridge assembly includes an actuation sled, a knife, and a cartridge body that supports pushers and staples. The firing actuator includes a flexible drive beam and a clamp member that is supported on a distal end of the flexible drive beam. The firing actuator is movable to advance the clamp member through the tool assembly to move the tool assembly from an open position to a clamped position, and to advance the actuation sled and knife through the cartridge body to eject the staples from the cartridge assembly and to cut tissue clamped between the anvil and cartridge assemblies.

Surgical stapling devices can be manually actuated devices or powered stapling devices. Powered stapling devices include one or more actuation buttons for activating a motor to initially advance the firing actuator and move the tool assembly from the open position to a clamped position, and subsequently advance the actuation sled and the knife through the tool assembly to fire the stapling device, i.e., eject staples from the cartridge assembly and cut tissue clamped between the cartridge and anvil assemblies. Such devices include a variety of different electronic devices to control operation of the motor including micro-controllers, rotary motor encoders, and software while others use mechanical devices including limit switches to control operation of the motor.

A continuing need exists in the art for a powered stapling device that includes a less complex, cost-effective device to control operation of the motor.

SUMMARY

This application is directed to a powered surgical device that includes a handle assembly having a linear position sensor in the form of a linear potentiometer for identifying a position of a rack within the handle assembly. The linear potentiometer provides a signal indicative of the position of the rack to a controller to control operation of a motor or motors positioned within the handle assembly to control various functions of the surgical device. The linear potentiometer supports a lever assembly that is coupled to a slide of the linear potentiometer to selectively couple and decouple the slide from the rack. The lever assembly facilitates the use of a linear potentiometer having a shorter length.

Aspects of the disclosure are directed to a powered handle assembly including a housing defining a cam slot, a rack, a drive assembly, a lever assembly, and a potentiometer. The rack is positioned within the housing and is movable between a rack retracted position and a rack advanced position. The drive assembly is engaged with the rack and is operable to move the rack between the rack retracted position and the rack advanced position. The lever assembly is supported on the rack and includes a lever having a cam member that is received in the cam slot of the housing. The lever is movable between a raised position and a lowered position. The potentiometer includes a body and a slide that is movable between a slide retracted position and a slide advanced position. The slide is positioned to be engaged by the lever when the lever is in the raised position such that movement of the rack causes movement of the slide.

In aspects of the disclosure, the rack defines an elongate slot, and the lever is received within the elongate slot.

In some aspects of the disclosure, the lever assembly includes a pivot member that pivotably couples the lever to the rack.

In certain aspects of the disclosure, the drive assembly includes a motor/gear assembly that includes a gear that is engaged with the rack, the motor/gear assembly operable to move the rack between the rack retracted position and the rack advanced position.

In aspects of the disclosure, the handle assembly includes a printed circuit board including a motor controller that is coupled to the potentiometer.

In some aspects of the disclosure, the rack is movable from the rack retracted position to a rack clamped position and from the rack clamped position to the rack advanced position, and the cam slot is configured to move the lever to the lowered position as the rack moves between the rack clamped position and the rack advanced position.

In certain aspects of the disclosure, the rack includes a proximal abutment, the proximal abutment positioned to engage the slide as the rack nears the rack advanced position to move the slide to the slide advanced position.

In aspects of the disclosure, the rack includes a distal abutment member that is positioned to engage the slide as the rack moves from the rack advanced position to the rack retracted position to move the slide back to the slide retracted position.

Other aspects of the disclosure are directed to a surgical device including a handle assembly, an elongate body, and a tool assembly. The handle assembly includes a housing defining a cam slot, a rack, a drive assembly, a lever assembly, and a potentiometer. The rack is positioned within the housing and is movable between a rack retracted position and a rack advanced position. The drive assembly is engaged with the rack and operable to move the rack between the rack retracted position and the rack advanced position. The lever assembly is supported on the rack and includes a lever having a cam member that is received in the cam slot of the housing. The lever is movable between a raised position and a lowered position. The potentiometer includes a body and a slide that is movable between a slide retracted position and a slide advanced position. The slide is positioned to be engaged by the lever when the lever is in the raised position such that movement of the rack causes movement of the slide. The elongate body extends distally from the from the handle assembly and includes a proximal portion, a distal portion, a control rod, and a firing actuator. The firing actuator includes a flexible beam and a working member secured to a distal portion of the flexible beam. The control rod has a proximal portion coupled to the rack and a distal portion coupled to the firing actuator. The tool assembly is supported on the distal portion of the elongate body.

In aspects of the disclosure, the tool assembly includes an anvil and a cartridge assembly, and the working member is movable through the tool assembly to move the tool assembly between an unclamped position and a clamped position and eject staples from the cartridge assembly.

Other aspects of the disclosure are directed to a powered handle assembly including a housing defining a cam slot, a rack, a drive assembly, a lever assembly, and a potentiometer. The rack is positioned within the housing and defines an elongate slot. The rack is movable between a rack retracted position and a rack advanced position. The drive assembly is engaged with the rack and is operable to move the rack between the rack retracted position and the rack advanced position. The lever assembly is supported on the rack within the elongate slot and includes a lever having a cam member that is received in the cam slot of the housing. The lever is movable between a raised position and a lowered position. The potentiometer includes a body and a slide that is movable between a slide retracted position and a slide advanced position. The slide is positioned to be engaged by the lever when the lever is in the raised position such that movement of the rack causes movement of the slide. The rack is movable from the rack retracted position to a rack clamped position and from the rack clamped position to the rack advanced position. The cam slot is configured to move the lever to the lowered position as the rack moves between the rack clamped position and the rack advanced position.

Other features of the disclosure will be appreciated from the following description.

BRIEF DESCRIPTION OF THE DRAWINGS

Various aspects of the disclosed surgical device are described herein below with reference to the drawings, wherein.

DETAILED DESCRIPTION

Figure 1:
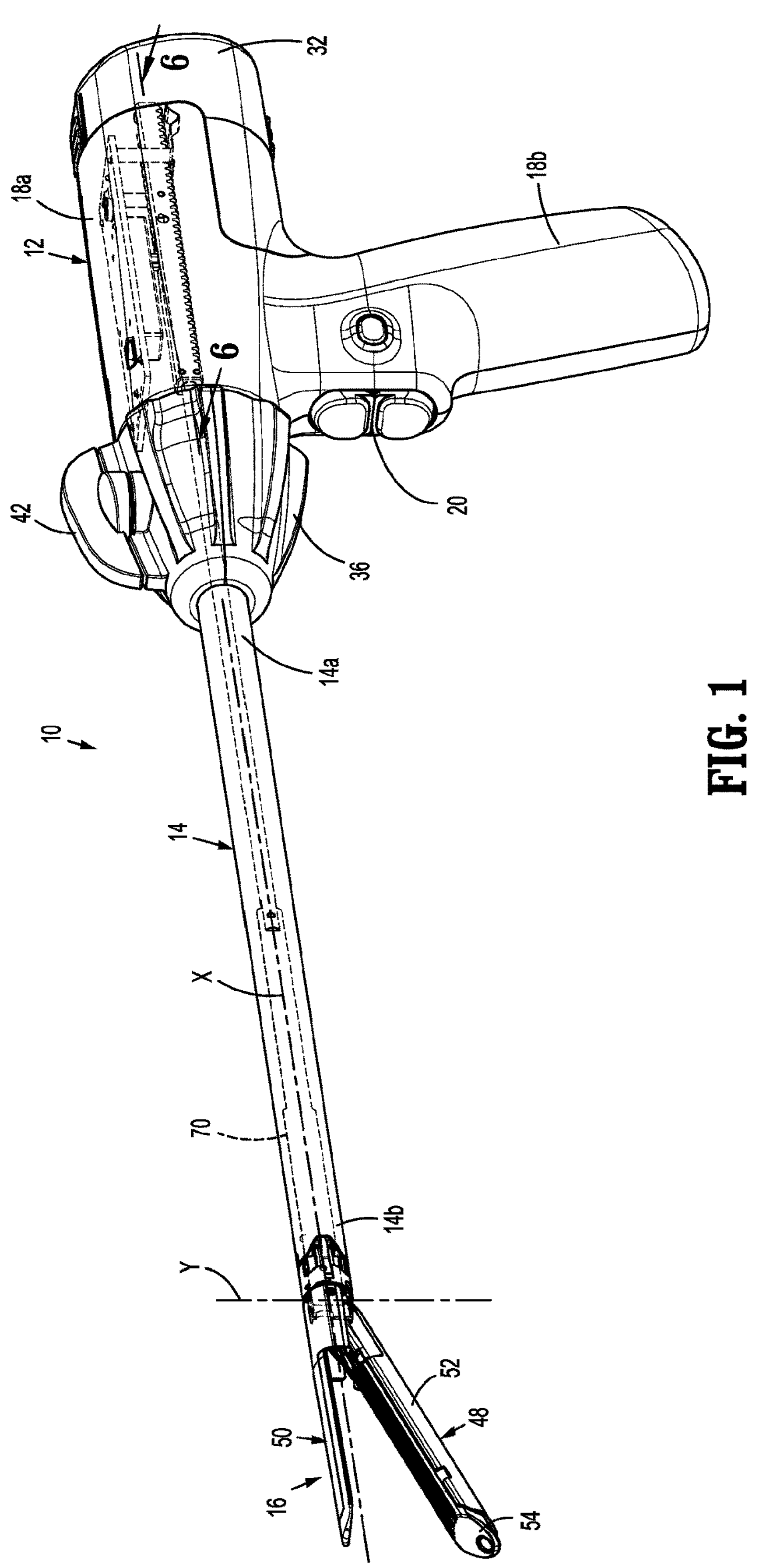
FIG. 1 is a side perspective view of a surgical device according to aspects of the disclosure in an unclamped, pre-fired position.

The disclosed surgical device will now be described in detail with reference to the drawings in which like reference numerals designate identical or corresponding elements in each of the several views. However, it is to be understood that the aspects of the disclosure are merely exemplary and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician when the device is used in its customary fashion, while the term "distal" is used generally to refer to that portion of the device that is farther from the clinician when the device is used in its customary fashion. In addition, the term "clinician" is used generally to refer to medical personnel including doctors, nurses, surgeons, and support personnel, and directional terms such as front, rear, upper, lower, top, bottom, and similar terms are used to assist in understanding the description and are not intended to limit the disclosure.

This disclosure is directed to a powered surgical device that includes a handle assembly that includes a linear position sensor in the form of a linear potentiometer for identifying a position of a rack within the handle assembly. The linear potentiometer provides a signal indicative of the position of the rack to a controller to control operation of a motor or motors positioned within the handle assembly to control various functions of the surgical device. The linear potentiometer supports a lever assembly that is coupled to a slide of the linear potentiometer to selectively couple and decouple the slide from the rack. The lever assembly facilitates the use of a linear potentiometer having a shorter length.

Figure 2:
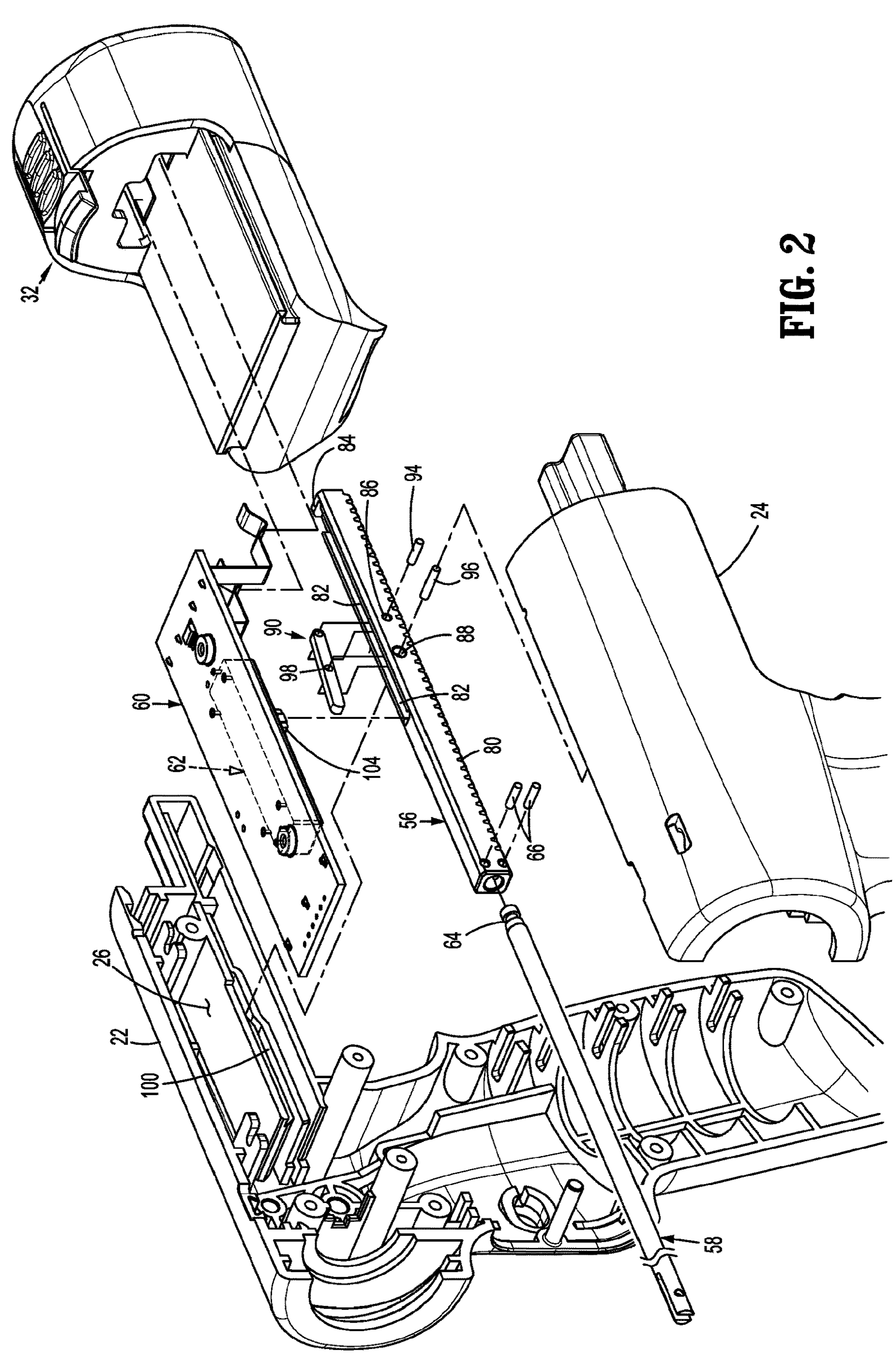
FIG. 2 is an enlarged view of internal components of a handle assembly of the surgical device that are shown in phantom in FIG. 1.

FIGS. 1 and 2 illustrate a surgical device shown generally as surgical device 10 which includes a powered handle assembly 12, an elongate body or adapter assembly 14, and a tool assembly 16. The handle assembly 12 includes a housing 18 that forms barrel 18*a* and a stationary handle portion 18*b* that extends downwardly from a central portion of the barrel 18*a*. In aspects of the disclosure, the housing 18 is formed from sections 22 and 24 (FIG. 2) that are secured together to define a cavity 26 (FIG. 2) that encloses internal components of the surgical device 10. In some aspects of the disclosure, the stationary handle portion 18*b* of the housing 18 supports an actuation button or buttons, e.g., a rocker 20, that can be actuated to control operation of the various functions of the stapling device 10, e.g., clamping, unclamping, and firing of the stapling device 10. The stationary handle portion 18*b* also supports or houses a drive assembly, e.g., motor/gear assembly 30 (FIG. 6), and the barrel 18*a* of the housing 18 supports a battery pack 32 (FIG. 2) which can be releasably coupled to the housing 18. The battery pack 32 and the motor/gear assembly 30 are positioned within the housing 18 to provide a balanced device to facilitate controlled manipulation of the surgical device 10. The battery pack 32 includes one or more batteries 32*a* (FIG. 7).

The elongate body 14 of the stapling device 10 has a proximal portion 14*a* and a distal portion 14*b* and defines a longitudinal axis "X". The proximal portion 14*a* of the elongate body 14 supports a rotation knob 36 and an articulation lever 42 that is supported on the rotation knob 36. The rotation knob 36 is coupled to the handle assembly 12 and supports the elongate body 14 to facilitate rotation of the elongate body 14 and the tool assembly 16 about the longitudinal axis "X" in relation to the handle assembly 12.

The tool assembly 16 is secured to the distal portion 14*b* of the elongate body 14 by a pivot member (not shown) that defines an articulation axis "Y" that is transverse to the longitudinal axis "X". The articulation lever 42 is operatively coupled to the tool assembly 16 via an articulation linkage (not shown) such that manipulation of the articulation lever 42 causes articulation of the tool assembly 16 about the pivot axis "Y" between a non-articulated position in which a longitudinal axis defined by the tool assembly 16 is aligned with the longitudinal axis "X" and articulated positions in which the longitudinal axis of the tool assembly 16 and the longitudinal axis "X" of the elongate body 14 are misaligned.

In aspects of the disclosure, the surgical device 10 is a surgical stapling device and the tool assembly 16 includes a cartridge assembly 48 and an anvil assembly 50. The cartridge assembly 48 includes a channel member 52 that supports a staple cartridge 54. In some aspects of the disclosure, the staple cartridge 54 is removably received in the channel member 52 and can be replaced after each firing of the stapling device 10 to facilitate reuse of the stapling device 10. In aspects of the disclosure, the channel member 52 is pivotably coupled to the anvil assembly 50 and is movable in relation to the anvil assembly 50 between unclamped and clamped positions. Alternately, the anvil assembly 50 can be pivotably coupled to the cartridge assembly 48 and movable in relation to the cartridge assembly 48 between unclamped and clamped positions.

Figure 3:
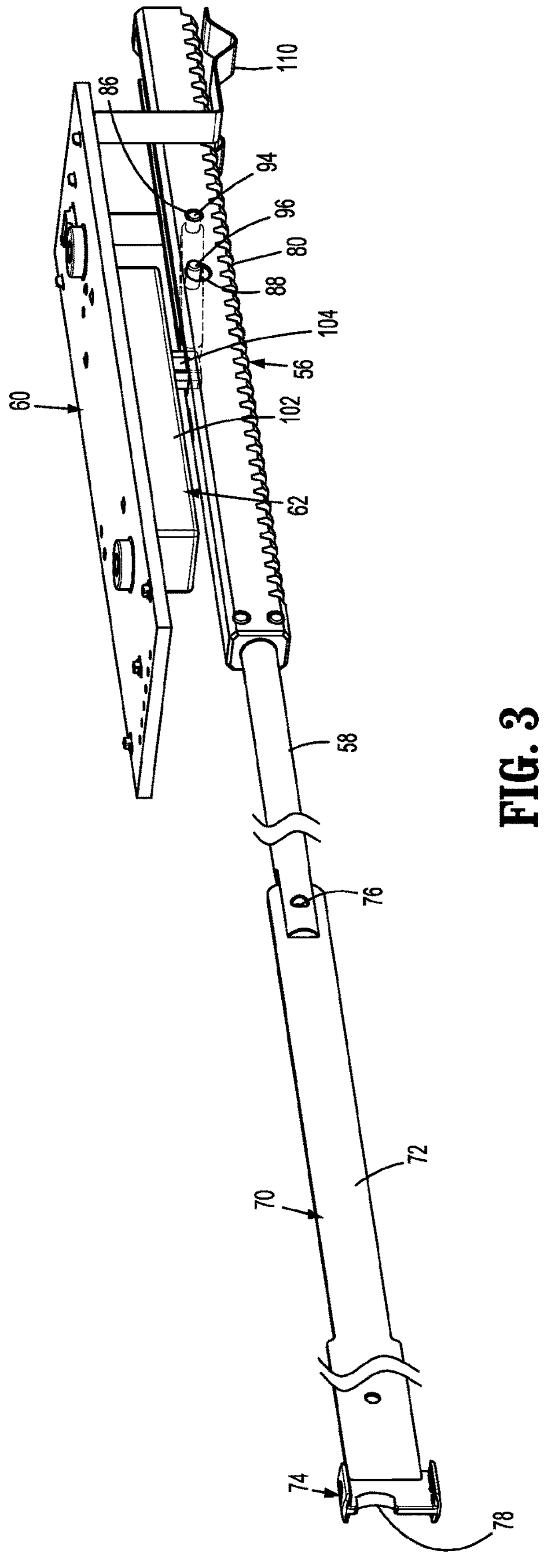
FIG. 3 is a side perspective view of the internal components of the surgical device that are shown in phantom in FIG. 1.
Figures 4, 5:
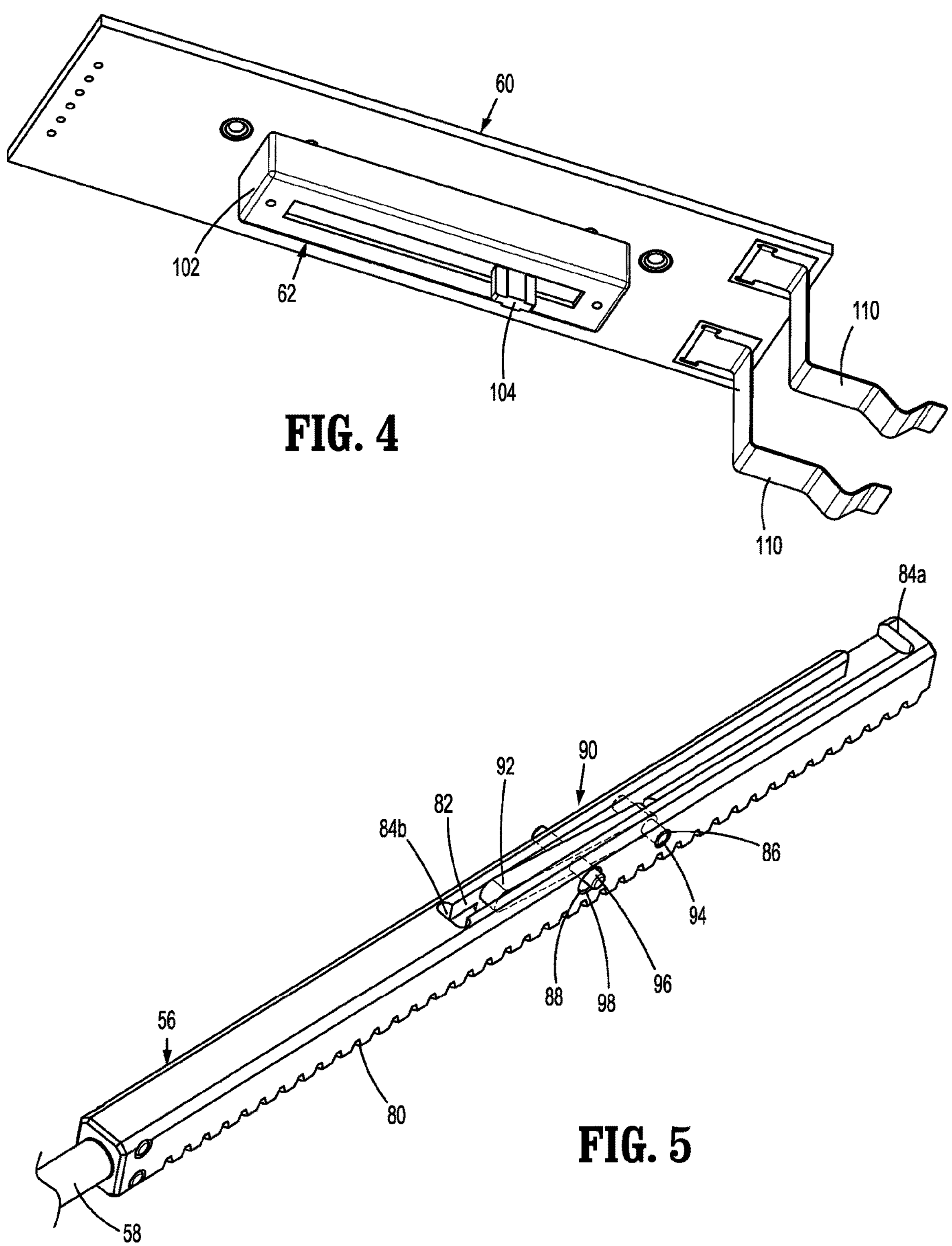
FIG. 4 is a bottom perspective view of a printed circuit board and potentiometer of the handle assembly of the surgical device shown in FIG. 1.
FIG. 5 is a perspective view from above of a rack and lever assembly of the handle assembly of the surgical device shown in FIG. 1.

FIGS. 2 and 3 illustrate internal components of the handle assembly 12 which includes a rack 56, a control rod 58, a printed circuit board ("PCB") 60, and a potentiometer 62. The rack 56 is supported within the housing 18 for longitudinal movement between retracted and advanced positions. The distal portion of the rack 56 is coupled to a proximal portion of the control rod 58 such that longitudinal movement of the rack 56 causes longitudinal movement of the control rod 58 within the elongate body 14 of the stapling device 10 (FIG. 1). In aspects of the disclosure, the proximal portion of the control rod 58 defines an annular recess 64 (FIG. 2) and the distal portion of the rack supports pins 66 that extend through the rack 56 and are received in the annular recess 64. The support pins 66 longitudinally fix the control rod 58 to the rack 56 while allowing the control rod 58 to rotate in relation to the rack 56.

The control rod 58 has a distal portion that is secured to a firing actuator 70 (FIG. 3). The firing actuator 70 includes a flexible drive beam 72 and a working member 74 secured to a distal portion of the flexible drive beam 72. In aspects of the disclosure, the flexible drive beam 72 of the firing actuator 70 is secured to the distal portion of the control rod 58 by a pin 76 (FIG. 3) such that longitudinal movement of the control rod 58 causes corresponding movement of the flexible drive beam 72. The working member 74 is secured to the distal portion of the flexible drive beam 72 such as by welding such that longitudinal movement of the drive beam 72 causes longitudinal movement of the working member 74. In some aspects of the disclosure, the working end 74 of the firing actuator 70 has an I-shaped configuration and includes a distally facing knife 78. The working end 74 of the firing actuator 70 is movable through the tool assembly 16 (FIG. 1) to move the tool assembly 16 between the unclamped and clamped positions and to eject staples (not shown) from the staple cartridge 54 of the cartridge assembly 48.

FIGS. 2-6 illustrate internal components of the handle assembly 12 (FIG. 1) including the rack 56, the potentiometer 62, and the PCB 60. The rack 56 includes a lower surface having gear teeth 80 that are engaged with a gear 112 (FIG. 6) of the motor/gear assembly 30 such that actuation of the motor/gear assembly 30 advances the rack 56 within the cavity 26 of the handle assembly 12 between the retracted and advanced positions. The upper surface of the rack 56 defines an elongate slot 82 and includes a proximal abutment 84*a* that is positioned adjacent the proximal end of the elongate slot 82 and a distal abutment 84*b* that is positioned adjacent the distal end of the elongate slot 82. The rack 56 defines a first through bore 86 and a second through bore 88 that communicate with the elongate slot 82.

The rack 56 supports a lever assembly 90 (FIG. 2) that includes a lever 92, a pivot pin 94, and a cam member 96. The lever 92 has a proximal portion that is pivotably secured within the elongate slot 82 by the pivot pin 94 which extends through the through bore 86 of the rack 56 and through the lever 92. The lever 92 defines a central bore 98. The cam member 96 extends through the through bore 88 of the rack 56 and through the central bore 98 of the lever 92 and is received in cam slots 100 (FIG. 2) (only one is shown) defined in the sections 22 and 24 (FIG. 2) of the housing 18. The through bore 88 in the rack 56 has a diameter that is larger than the diameter of the cam member 96 such that the cam member 96 is movable within the through bore 88 to move the lever 92 between a lowered position in which the lever 92 is recessed within the elongate slot 82 of the rack 56 and a raised position in which a distal end of the lever 92 extends upwardly from the elongate slot 82 of the rack 56.

Figure 5A:
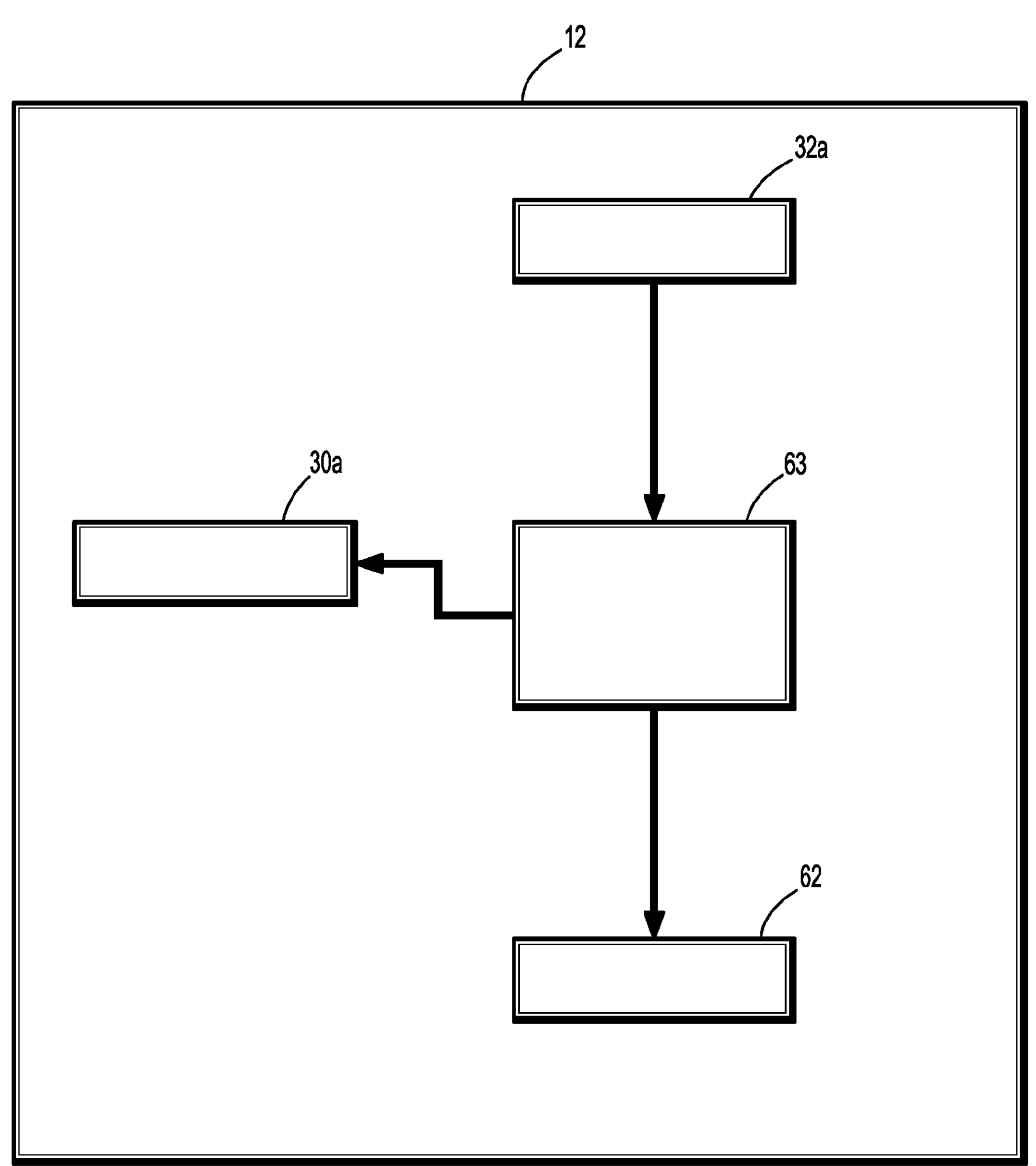
FIG. 5A is a schematic view of the control circuitry of the handle assembly of the surgical device shown in FIG. 1.

The PCB 60 is supported within the housing 18 at a position above the rack 56 and supports the potentiometer 62. The potentiometer 62 includes body 102 and a slide 104 that is movable along the body 102. The slide 104 is received within the elongate slot 82 of the rack 56 and is engaged with the distal end of the lever 92 when the rack 56 is in the retracted position. The potentiometer 62 is electrically coupled to a motor driver or controller 63 on the PCB 60 and inputs signals generated based on the position of the slide 104 on the potentiometer 62 into a motor controller 63 (FIG. 5A) to control forward and reverse motion of the motor 30*a* of the motor/gear assembly 30. The signals provide status information to the controller 63 regarding position of the rack 56 within the handle assembly 12 and other mechanical components of the stapling device 10. In aspects of the disclosure, the motor 30*a* (FIG. 6) of the motor/gear assembly 30 includes a DC brushed motor although other types of motors are envisioned. In some aspects of the disclosure, the potentiometer 62 may be coupled to the controller 63 via logical gate circuits. The PCB 60 includes electrical contacts 110 that are supported on the proximal portion of the PCB 60 and engage contacts (not shown) of the battery pack 32 (FIG. 2) to electrically couple the PCB 60 to the battery pack 32.

The slide 104 of the potentiometer 62 is engaged with the rack 56 to track movement of the rack 56 from the retracted position of the rack 56 to the advanced position of the rack 56. To reduce the length of the potentiometer 62 and minimize the length of the barrel 18*a* of the housing 18, the lever assembly 90 disengages the slide 104 of the potentiometer 62 from the rack 56 during the firing stroke of the surgical device 10 (FIG. 1). In aspects of the disclosure, the total travel distance of the rack 56 from the retracted position to the advanced position is about 70 mm, whereas the length of the potentiometer 62 is about 30 mm. It is envisioned that the configuration of the cam slots 100 (FIG. 2) in the sections 22, 24 of the housing 18 can be modified to accommodate a variety of different length racks 56 and potentiometers 62.

Figure 6:
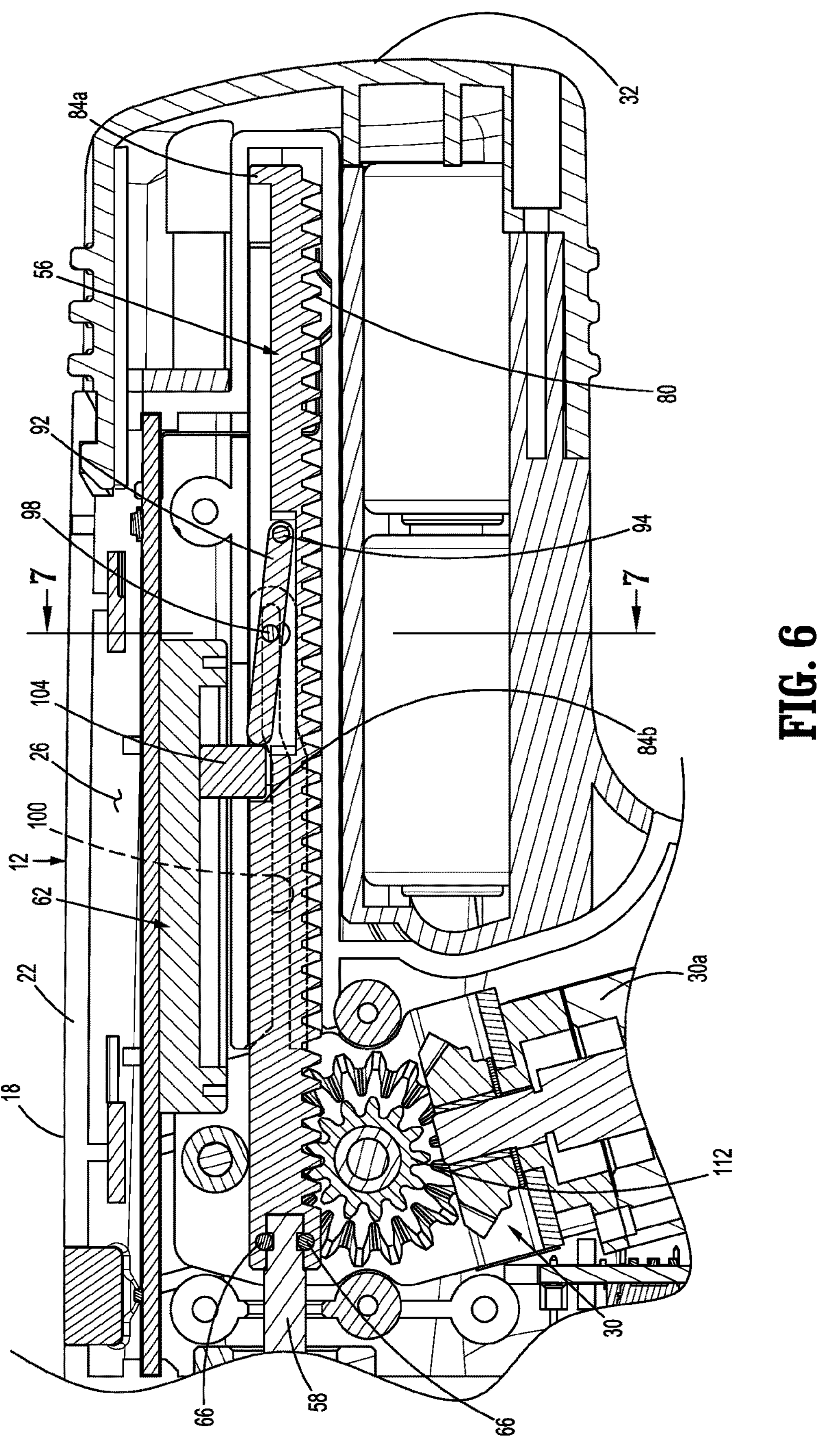
FIG. 6 is a cross-sectional view taken along section line 6-6 of FIG. 1.
Figure 7:
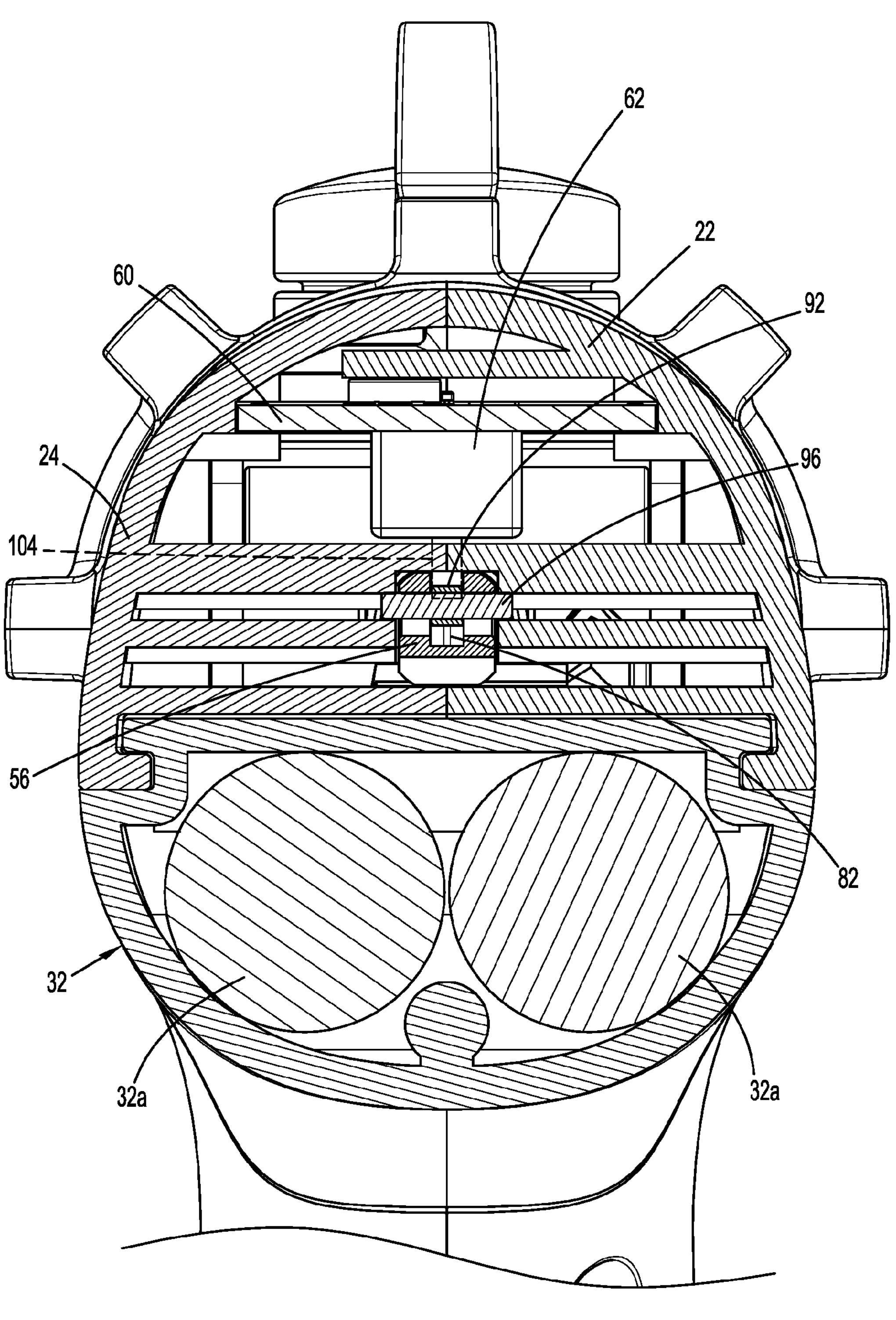
FIG. 7 is a cross-sectional view taken along section line 7-7 of FIG. 6.

FIGS. 6 and 7 illustrate the handle portion 12 of the surgical device 10 (FIG. 1) with the rack 56 in the retracted position and the surgical device 10 (FIG. 1) in an unclamped position. In the retracted position of the rack 56, the slide 104 of the potentiometer 62 is positioned on a proximal portion of the body 102, and the lever 92 of the lever assembly 90 is in the raised position engaged with the slide 104. The cam member 96 of the lever assembly 90 is received in the cam slots 100 (FIG. 2) of the housing 18.

Figures 8, 9:
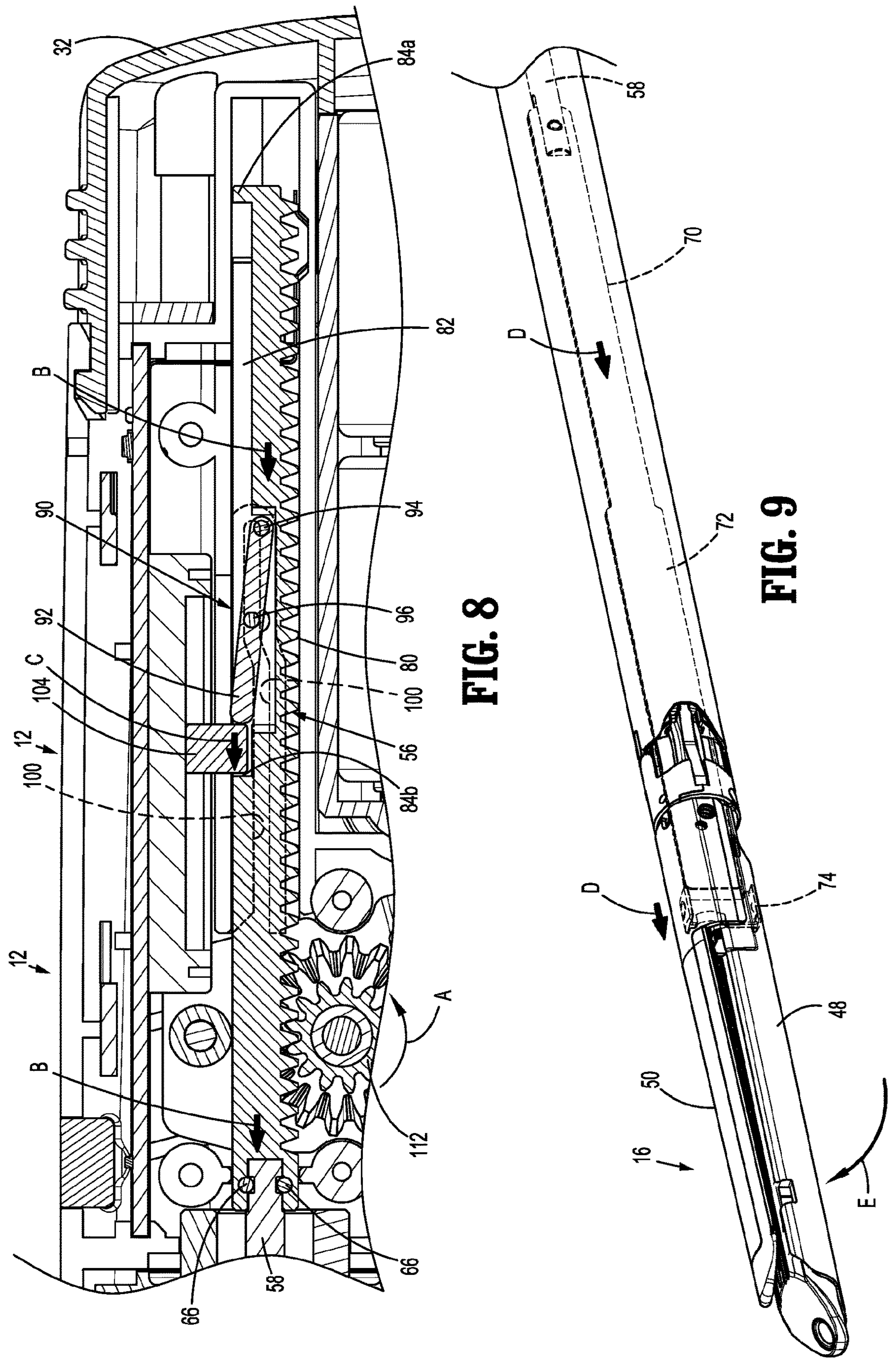
FIG. 8 is a cross-sectional view taken through the handle assembly of the surgical device shown in FIG. 1 with the surgical device in a clamped position.
FIG. 9 is a side perspective view of a distal portion of the surgical device with a tool assembly of the surgical device in the clamped position.

FIGS. 8 and 9 illustrate the surgical device 10 as the rack 56 is advanced from the retracted position towards the advanced position to move the tool assembly 16 (FIG. 9) from the unclamped position to the clamped position. When the actuation button 20 (FIG. 1) is depressed to move the surgical device 10 (FIG. 1) to the clamped position, the gear 112 of the motor/gear assembly 30 which is engaged with the gear teeth 80 of the rack 56 is rotated in the direction of arrow “A” in FIG. 8 to advance the rack 56 in the direction of arrow “B” in FIG. 8. As the rack 56 moves in the direction of arrows “B”, the lever 92 of the lever assembly 90 which is pivotably supported on the rack 56 by the pivot pin 94 moves with the rack 56. In the retracted position, the cam member 96 of the lever assembly 90 is positioned in proximal portions of the cam slots 100 to position the lever 92 in the raised position. In the raised position, the distal end of the lever 92 is engaged with the slide 104 of the potentiometer 62 such that movement of the rack 56 in the direction of arrows “B” causes distal movement of the slide 104 in the direction of arrow “C” in FIG. 8 along the body 102 of the potentiometer 62.

As the rack 56 moves in the direction of arrows “B” in FIG. 8, the control rod 58 and the firing actuator 70 are moved in the direction of arrow “D” in FIG. 9 to move the working member 74 of the firing actuator 70 through the tool assembly 16 in the direction of arrow “D” in FIG. 9. As the working member 74 of the firing actuator 70 moves through the tool assembly 16, the cartridge assembly 48 of the tool assembly 16 is pivoted in the direction of arrow “E” in FIG. 9 towards the anvil assembly 50 to move the tool assembly 16 from the unclamped position to the clamped position. When the rack 56 moves towards the advanced position to move the tool assembly 16 from the unclamped position to the clamped position, the position of the slide 104 on the body 102 of the potentiometer 62 causes a signal to be sent to the motor controller 63 (FIG. 5A) to stop operation of the motor/gear assembly 30 (FIG. 6).

Figures 10, 11:
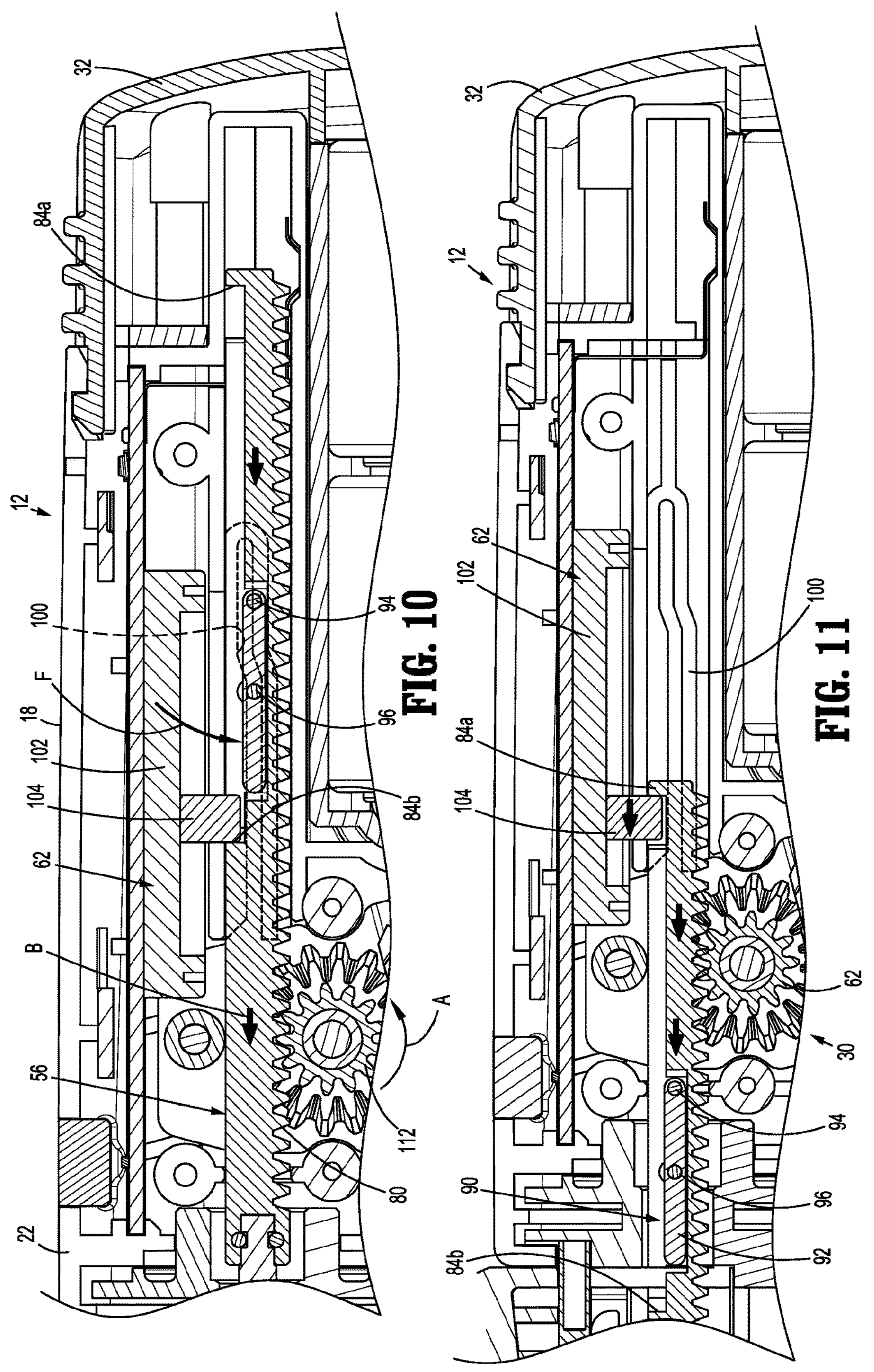
FIG. 10 is a cross-sectional view taken through the handle assembly of the surgical device shown in FIG. 1 as the surgical device is being fired as the potentiometer is moved to a disengaged position.
FIG. 11 is a cross-sectional view taken through the handle assembly of the surgical device shown in FIG. 1 with the surgical device in a fired position.

FIG. 10 illustrates the handle assembly 12 of the surgical device 10 (FIG. 1) as the rack 56 is advanced from the intermediate or clamped position towards the advanced position to fire the surgical device 10. When the actuation button 20 (FIG. 1) is depressed to fire the surgical device 10 (FIG. 1), the gear 112 of the motor/gear assembly 30 is rotated in the direction of arrow “A” to advance the rack 56 further in the direction of arrow “B” towards the advanced position. As the rack 56 moves in the direction of arrow “B”, the cam member 96 of the lever assembly 90 moves within the cam slots 100 (FIG. 2) of the housing 18 to pivot the lever 92 downwardly in the direction of arrow “F” to the lowered position to disengage the lever 92 from the slide 104 of the potentiometer 62. Once the lever 92 of the lever assembly 90 is moved to the lowered position, the rack 56 moves towards the advanced position independently of the slide 104 of the potentiometer 62. As the rack 56 moves towards the advanced position, the working end 74 of the firing actuator 70 moves through the tool assembly 16 to eject staples (not shown) from the staple cartridge 54 of the cartridge assembly 48.

Figures 12, 13:
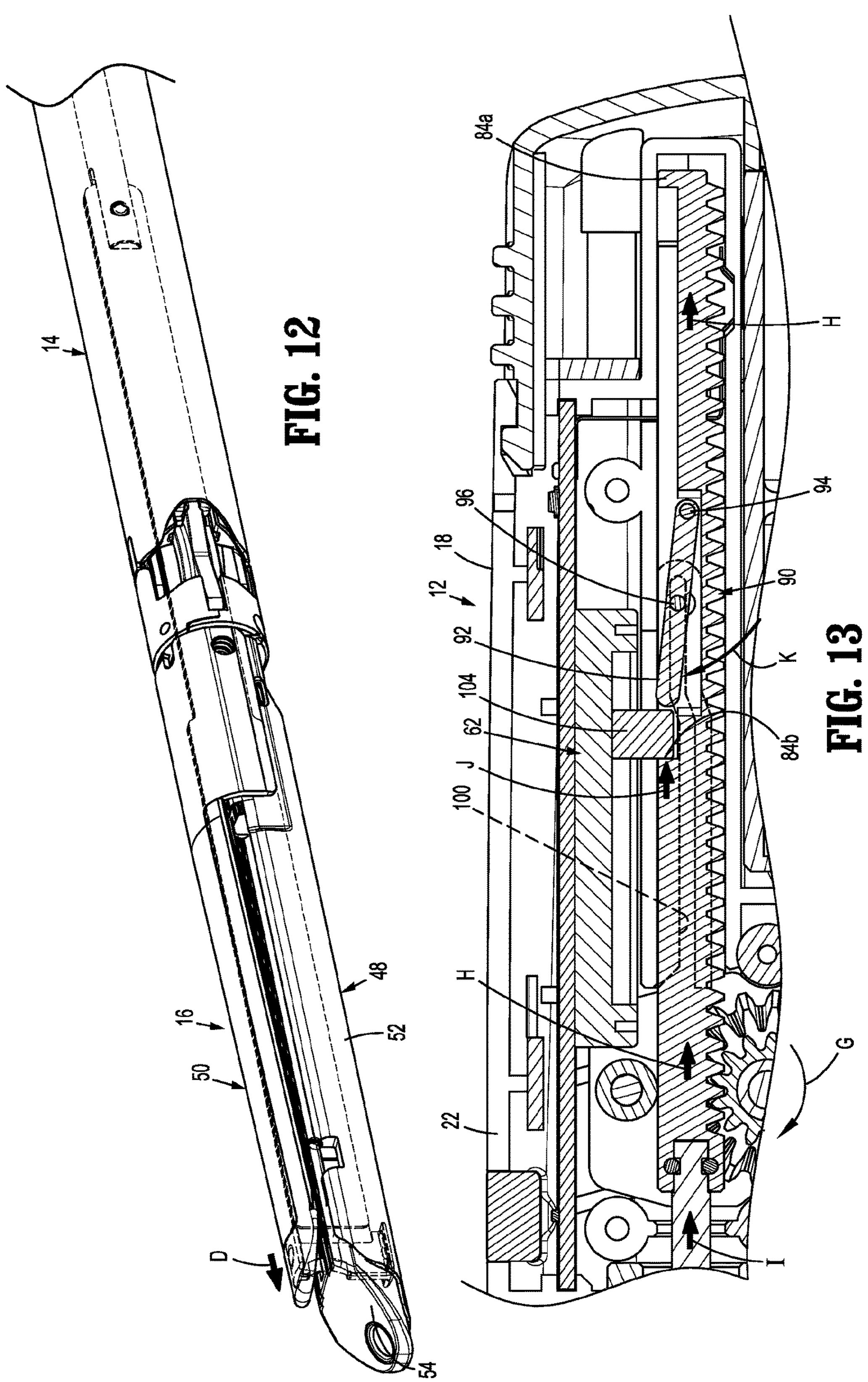
FIG. 12 is a side perspective view of the distal portion of the surgical device with the tool assembly of the surgical device in the fired position.
FIG. 13 is a cross-sectional view taken through the handle assembly of the surgical device shown in FIG. 1 with the surgical device in a retracted position after the surgical device is fired.

FIGS. 11 and 12 illustrate the handle assembly 12 of the surgical device 10 (FIG. 1) as the rack 56 nears the advanced position to complete firing of the surgical device 10. When the rack 56 nears the advanced position, the proximal abutment 84*a* on the rack 56 engages the slide 104 of the potentiometer 62 to advance the slide 104 to a position on the body 102 of the potentiometer 62 that causes a signal to be sent to the motor controller to stop operation of the motor/gear assembly 30 (FIG. 6). The position of the slide 104 of the potentiometer 62 can also provide a signal to initiate automatic retraction of the rack 56. It is envisioned that retraction of the rack 56 can require manual actuation of the actuation button 20.

FIG. 13 illustrates the handle assembly 12 as the rack 56 returns to the retracted position after the surgical device 10 (FIG. 1) is fired. After the firing actuator 70 is moved to the advanced position and firing is completed, the gear 112 of the motor/gear assembly 30 is rotated in the direction of arrow “G” to return the rack 56 in the direction of arrow “H” from the advanced position to the retracted position. As the rack 56 returns to the retracted position in the direction of arrow “H”, the firing actuator 70 is moved proximally in the direction of arrow “I” to move the tool assembly 16 back to the unclamped position (FIG. 1). As the rack 56 moves towards the retracted position, the distal abutment 84*b* on the rack 56 engages the slide 104 of the potentiometer 62 to move the slide 104 of the potentiometer 62 in the direction of arrow “J” back to the retracted position of the slide 104, and the cam member 96 of the lever assembly 90 moves within the cam slots 100 of the housing 18 to pivot the lever 92 of the slide assembly 90 in the direction of arrow “K” from the lowered position to the raised position. In the raised position, the lever 92 is positioned proximal to the slide 104 of the potentiometer 62 such that the handle assembly 12 is positioned to perform another stapling operation.

When the distal abutment 84*b* engages the slide 104 and returns the slide 104 to its retracted position, the position of the slide 104 on the body 102 of the potentiometer 62 causes a signal to be sent to the motor controller to stop operation of the motor/gear assembly 30 (FIG. 6).

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A powered handle assembly comprising:
- a housing defining a cam slot;
- a rack positioned within the housing, the rack movable between a rack retracted position and a rack advanced position;
- a drive assembly engaged with the rack and operable to move the rack between the rack retracted position and the rack advanced position;
- a lever assembly supported on the rack and including a lever, the lever including a cam member that is received in the cam slot of the housing, the lever being movable between a raised position and a lowered position; and
- a potentiometer including a body and a slide, the slide movable between a slide retracted position and a slide advanced position, the slide positioned to be engaged by the lever when the lever is in the raised position such that movement of the rack causes movement of the slide.

2. The powered handle assembly of claim 1, wherein the rack defines an elongate slot, and the lever is received within the elongate slot.

3. The powered handle assembly of claim 2, wherein the lever assembly includes a pivot member that pivotably couples the lever to the rack.

4. The powered handle assembly of claim 3, wherein the drive assembly includes a motor/gear assembly that includes a gear that is engaged with the rack, the motor gear assembly operable to move the rack between the rack retracted position and the rack advanced position.

5. The powered handle assembly of claim 4, wherein the handle assembly includes a printed circuit board that is coupled to the potentiometer.

6. The powered handle assembly of claim 5, wherein the rack is movable from the rack retracted position to a rack clamped position and from the rack clamped position to the rack advanced position, and the cam slot is configured to move the lever to the lowered position as the rack moves between the rack clamped position and the rack advanced position.

7. The powered handle assembly of claim 6, wherein the rack includes a proximal abutment, the proximal abutment positioned to engage the slide as the rack nears the rack advanced position to move the slide to the slide advanced position.

8. The powered handle assembly of claim 6, wherein the rack includes a distal abutment member that is positioned to engage the slide as the rack moves from the rack advanced position to the rack retracted position to move the slide back to the slide retracted position.

9. A surgical device comprising:
- a handle assembly including:
  - a housing defining a cam slot;
  - a rack positioned within the housing, the rack movable between a rack retracted position and a rack advanced position;
  - a drive assembly engaged with the rack and operable to move the rack between the rack retracted position and the rack advanced position;
  - a lever assembly supported on the rack and including a lever, the lever including a cam member that is received in the cam slot of the housing, the lever being movable between a raised position and a lowered position; and
  - a potentiometer including a body and a slide, the slide movable between a slide retracted position and a slide advanced position, the slide positioned to be engaged by the lever when the lever is in the raised position such that movement of the rack causes movement of the slide;
- an elongate body extending distally from the from the handle assembly, the elongate body including a proximal portion, a distal portion, a control rod, and a firing actuator, the firing actuator including a flexible beam and a working member secured to a distal portion of the flexible beam, the control rod having a proximal portion coupled to the rack and a distal portion coupled to the firing actuator; and
- a tool assembly supported on the distal portion of the elongate body.

10. The surgical device of claim 9, wherein the tool assembly includes an anvil and a cartridge assembly, the working member movable through the tool assembly to move the tool assembly between unclamped and clamped positions and eject staples from the cartridge assembly.

11. The surgical device of claim 9, wherein the rack of the handle assembly defines an elongate slot, and the lever is received within the elongate slot.

12. The surgical device of claim 11, wherein the lever assembly includes a pivot member that pivotably couples the lever to the rack.

13. The surgical device of claim 12, wherein the drive assembly includes a motor/gear assembly that includes a gear that is engaged with the rack, the motor gear assembly operable to move the rack between the rack retracted position and the rack advanced position.

14. The surgical device of claim 13, wherein the handle assembly includes a printed circuit board that is coupled to the potentiometer.

15. The surgical device of claim 14, wherein the rack is movable from the rack retracted position to a rack clamped position and from the rack clamped position to the rack advanced position, and the cam slot is configured to move the lever to the lowered position as the rack moves between the rack clamped position and the rack advanced position.

16. The surgical device of claim 15, wherein the rack includes a proximal abutment, the proximal abutment positioned to engage the slide as the rack nears the advanced position to move the slide to a slide advanced position.

17. The surgical device of claim 15, wherein the rack includes a distal abutment member that is positioned to engage the slide as the rack moves from the advanced position to the retracted position.

18. A powered handle assembly comprising:
- a housing defining a cam slot;
- a rack positioned within the housing, the rack defining an elongate slot and being movable between a rack retracted position and a rack advanced position;

a drive assembly engaged with the rack and operable to move the rack between the rack retracted position and the rack advanced position;

a lever assembly supported on the rack within the elongate slot, the lever assembly including a lever having a cam member that is received in the cam slot of the housing, the lever movable between a raised position and a lowered position; and a potentiometer including a body and a slide, the slide movable between a slide retracted position and a slide advanced position, the slide positioned to be engaged by the lever when the lever is in the raised position such that movement of the rack causes movement of the slide, wherein the rack is movable from the rack retracted position to a rack clamped position and from the rack clamped position to the rack advanced position, and the cam slot is configured to move the lever to the lowered position as the rack moves between the rack clamped position and the rack advanced position.

19. The powered handle assembly of claim 18, wherein the lever assembly includes a pivot member that pivotably couples the lever to the rack.

20. The powered handle assembly of claim 19, wherein the rack includes a proximal abutment that is positioned to engage the slide as the rack nears the advanced position to move the slide to a slide advanced position, and the rack includes a distal abutment member that is positioned to engage the slide as the rack moves from the advanced position to the retracted position to move the slide towards the slide retracted position.

* * * * *